(12) United States Patent
Kuo

(10) Patent No.: US 9,826,866 B2
(45) Date of Patent: Nov. 28, 2017

(54) PORTABLE URINAL

(71) Applicant: Han Kuo, Alhambra, CA (US)

(72) Inventor: Han Kuo, Alhambra, CA (US)

(*) Notice: Subject to any disclaimer, the term of this patent is extended or adjusted under 35 U.S.C. 154(b) by 0 days.

(21) Appl. No.: 15/011,632

(22) Filed: Jan. 31, 2016

(65) Prior Publication Data

US 2017/0215661 A1   Aug. 3, 2017

(51) Int. Cl.
| | |
|---|---|
| A47K 11/00 | (2006.01) |
| A47K 11/12 | (2006.01) |
| A61F 5/453 | (2006.01) |
| A61F 5/455 | (2006.01) |

(52) U.S. Cl.
CPC ............. *A47K 11/12* (2013.01); *A61F 5/453* (2013.01); *A61F 5/4556* (2013.01)

(58) Field of Classification Search
CPC ...................................... A61G 9/006
USPC ................................. 4/144.1–144.3
See application file for complete search history.

(56) References Cited

U.S. PATENT DOCUMENTS

| | | | | |
|---|---|---|---|---|
| 3,030,636 A * | 4/1962 | Evans | ............... | A61G 9/006 4/144.3 |
| 6,021,531 A * | 2/2000 | Kirko | ............... | A47K 11/12 4/144.1 |
| 6,212,691 B1 * | 4/2001 | Heberer | ............... | A47K 11/12 4/144.1 |
| 6,684,414 B1 * | 2/2004 | Rehrig | ............... | A47K 11/12 4/144.1 |
| 7,435,242 B2 * | 10/2008 | Levinson | ............... | A61B 10/007 4/144.1 |
| 7,846,143 B1 * | 12/2010 | Abbato | ............... | A61G 9/006 137/512.15 |
| 8,181,284 B1 * | 5/2012 | Parker | ............... | B60R 15/04 4/144.3 |
| 8,650,669 B1 * | 2/2014 | Kolter | ............... | A47K 11/12 4/144.1 |
| 2012/0210503 A1 * | 8/2012 | Anzivino, Sr. | ....... | A61F 5/4556 4/144.3 |
| 2014/0033414 A1 * | 2/2014 | Kolter | ............... | A47K 11/12 4/144.3 |
| 2015/0320628 A1 * | 11/2015 | Sands | ............... | A61G 9/006 4/144.3 |

* cited by examiner

*Primary Examiner* — Lori Baker
(74) *Attorney, Agent, or Firm* — Tsz Lung Yeung

(57) ABSTRACT

A portable urinal is arranged for coupling with a bottle having a bottle opening, wherein the portable urinal includes an urine collector having a funnel channel for receiving urine expelled by a user, and an attachment head including a detachable lid extended from the urine collector for detachably coupling at the bottle opening of the bottle, and a tubular urinal guider extended from the detachable lid for inserting into the bottle opening of the bottle when the detachable lid is coupled at the bottle opening of the bottle so as to guide the urine into the bottle from the funnel channel. After use, the portable urinal is detached from the bottle and a bottle cap is re-placed at the bottle opening to seal the urine in the bottle.

10 Claims, 5 Drawing Sheets

PORTABLE URINAL

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

Field of Invention

The present invention relates to an urinal apparatus, and more particularly to a portable urinal, which is a portable unisex urinal apparatus for guiding a user's urinary waste matters into a bottle.

Description of Related Arts

Portable urinal is known as a bed urinal for a patient confined to a hospital bed. Nowadays, people carry the portable urinal for travel use. The portable urinal generally comprises a bowl shaped container having an elongated neck portion and an opening formed thereat. The portable urinal further comprises a lid member coupled at the container to selectively close and seal the opening for preventing the urine from being leaked.

However, the existing portable urinal has several drawbacks. After use, urine is fully contained in the portable urinal. It is a hassle to manage the portable urinal when the container is full of urine. Even though the lid member can seal the opening of the container, the urine may accidentally spilled out of the container when the container is tipped or kicked over. It is inconvenient and unsanitary to clean the urinal on the floor, especially in the vehicle during traveling. Furthermore, after the first time use, the portable urinal should not be re-used for hygiene issue even the neck portion is cleaned and sanitized. In other words, the portable urinal is considered as a onetime use device.

SUMMARY OF THE PRESENT INVENTION

The invention is advantageous in that it provides a portable urinal, which is a portable unisex urinal apparatus for guiding a user's urinary waste matters into a bottle.

Another advantage of the invention is to provide a portable urinal, wherein the attachment head to the disposable bottle is secured for preventing the spillage problem during the portable urinal is being used.

Another advantage of the invention is to provide a portable urinal, wherein the tubular urinal guider of the attachment head is long enough to extend into the bottle opening of the bottle in order to guide the urine into the bottle, such that the bottle opening of the bottle is not contacted with any urine during use. Therefore, it is sanitary for the user put the bottle cap back to the bottle to close and seal the bottle opening thereof.

Another advantage of the invention is to provide a portable urinal, wherein the diameter of the urinal guider is slightly smaller than the diameter of the bottle opening of the bottle, such that after the urinal guider is inserted through the bottle opening, the urinal guider not only guides the urine into the bottle but also serves as a shaft to support the urinal collector at the bottle.

Another advantage of the invention is to provide a portable urinal, wherein the bottle retainer is forwardly extended for biasing against an exterior wall of the bottle to prevent an unintentional movement between the urine collector and the bottle.

Another advantage of the invention is to provide a portable urinal, which can fit to any disposable bottle, such as water bottle, such that the user is able to easily find or save any used disposable bottle in order to utilize the portable urinal with the bottle.

Another advantage of the invention is to provide a portable urinal, which is easy to manufacture in low cost by plastic mold injection. The portable urinal can also be made of disposable and/or re-cycling material.

Another advantage of the invention is to provide a portable urinal, which does not require to alter the original structural design of the bottle, so as to enhance the practical use of the portable urinal to incorporate with any existing bottle, urine collecting cup, and/or disposable cup.

Another advantage of the invention is to provide a portable urinal, wherein no expensive or complicated structure is required to employ in the present invention in order to achieve the above mentioned objects. Therefore, the present invention successfully provides an economic and efficient solution for providing a simple urine collecting configuration for the collecting urine in the bottle in a convenient and sanitary manner.

Additional advantages and features of the invention will become apparent from the description which follows, and may be realized by means of the instrumentalities and combinations particular point out in the appended claims.

According to the present invention, the foregoing and other objects and advantages are attained by a portable urinal for coupling with a bottle having a bottle opening, wherein the portable urinal comprises an urine collector having a funnel channel for receiving urine expelled by a user, and an attachment head comprising a detachable lid extended from the urine collector for detachably coupling at the bottle opening of the bottle, and a tubular urinal guider extended from the detachable lid for inserting into the bottle opening of the bottle when the detachable lid is coupled at the bottle opening of the bottle so as to guide the urine into the bottle from the funnel channel. After use, the portable urinal is detached from the bottle and a bottle cap is re-placed at the bottle opening to seal the urine in the bottle.

Still further objects and advantages will become apparent from a consideration of the ensuing description and drawings.

These and other objectives, features, and advantages of the present invention will become apparent from the following detailed description, the accompanying drawings, and the appended claims.

DETAILED DESCRIPTION OF THE PREFERRED EMBODIMENT

The following description is disclosed to enable any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

Figure 1:
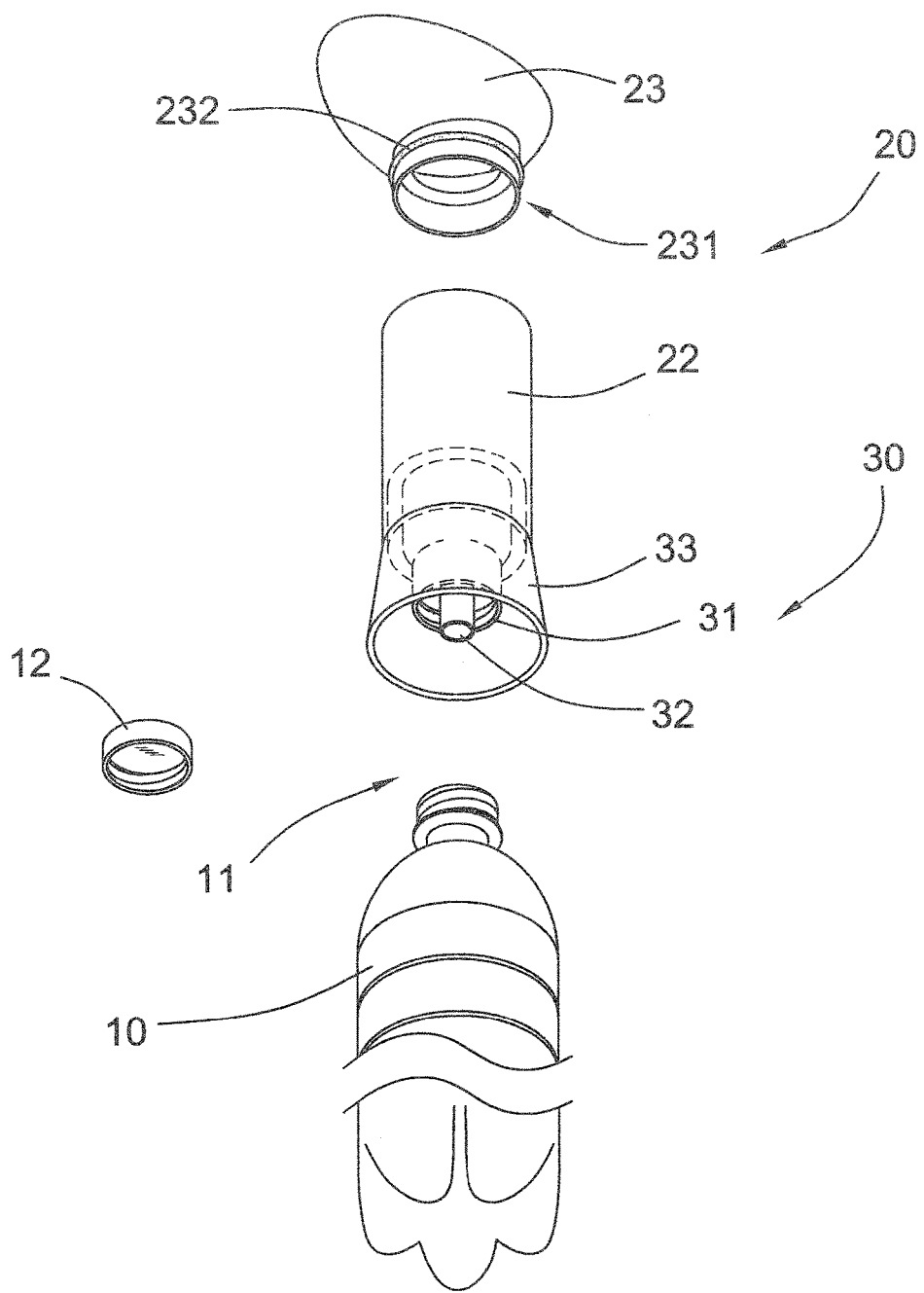
FIG. 1 is a perspective view of a portable urinal according to a preferred embodiment of the present invention.
Figure 2:
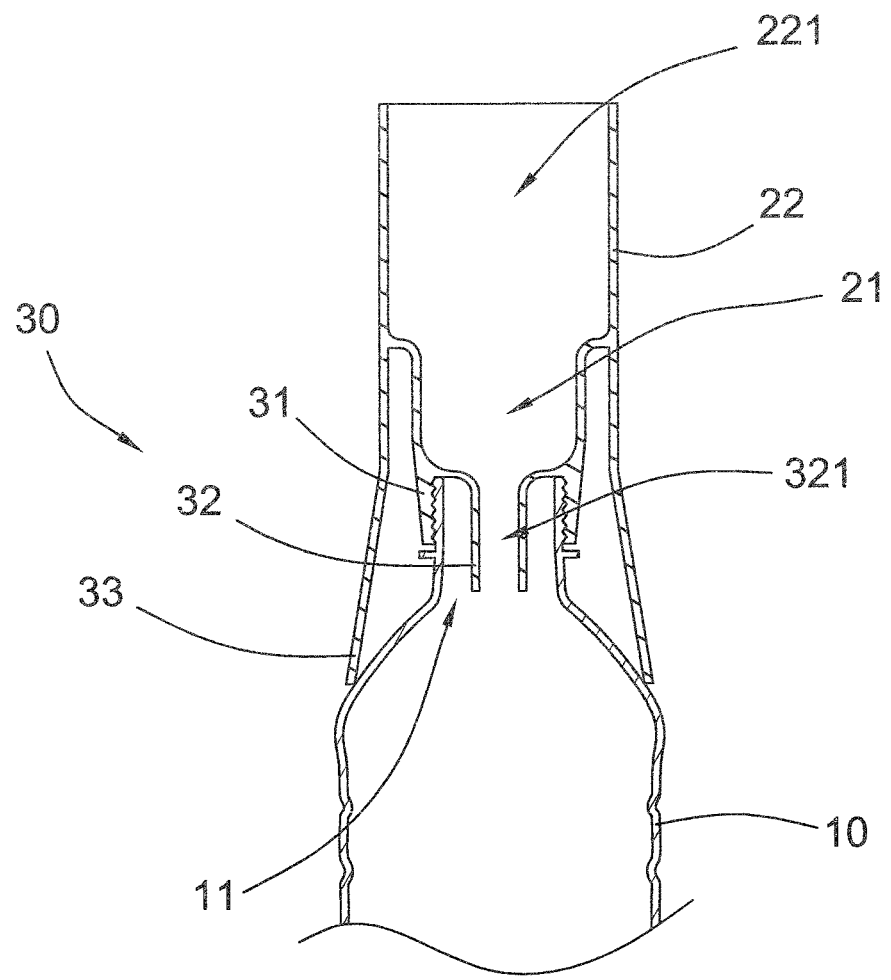
FIG. 2 is a sectional view of the portable urinal according to the above preferred embodiment of the present invention.

Referring to FIGS. 1 and 2, a portable urinal according to a preferred embodiment of the present invention, wherein the portable urinal is arranged for detachably coupling with a bottle 10. Accordingly, the bottle 10, such as a disposable bottle, water bottle, or the like, generally has a bottle opening 11 and a bottle cap 12. According to the preferred embodiment, the portable urinal comprises an urine collector 20 and an attachment head 30.

The urine collector 20 has a funnel channel 21 for receiving urine expelled by a user. The urine collector 20 defines a front end and a rear end, wherein the funnel channel 21 has two open ends and has a diameter gradually reducing from the rear end to front end. The urine collector 20 further comprises a tubular handheld member 22 having an elongated urine channel 221 and defining a portion integrated with the funnel channel 21. Accordingly, the handheld member 22 is arranged for being held at an urinating orifice of the male user. Preferably, the handheld member 22 has an elongated configuration that the urine channel 221 has a uniform diameter, such that the user is able to hold and grip the handheld member 22 close to the urinating orifice of the user. The urine collector 20 further comprises a funnel member 23 detachably coupled at the handheld member 22 for being placed at the urinating orifice of the female user. Preferably, the funnel member 23 has a tubular inserting portion 231 detachably inserted into the handheld member 22 and a sealing element 232 encircled around the inserting portion 231 to water-seal the inserting portion 231 of the funnel member 23 within an inner annular wall of the handheld member 22. It is appreciated that the funnel member 23 can be integrally extended from the handheld member 22 as a one piece integrated urine collector.

The attachment head 30 comprises a detachable lid 31 extended from the urine collector 20 for detachably coupling at the bottle opening 11 of the bottle 10, and a tubular urinal guider 32 extended from the detachable lid 31 for inserting into the bottle opening 11 of the bottle 10 when the detachable lid 31 is coupled at the bottle opening 11 of the bottle 10 so as to guide the urine into the bottle 10 from the funnel channel 21. In particular, the urine is guided to flow from the urine channel 221 to the funnel channel 21, and is then guided to flow into the bottle 10 through the urinal guider 32. After use, the portable urinal is detached from the bottle 10 and a bottle cap 12 is re-placed at the bottle opening 11 to seal the urine in the bottle 10.

According to the preferred embodiment, the detachable lid 31 has an attachment configuration similar than an attachment configuration of the bottle cap 12 of the bottle 10. In particular, the detachable lid 31 is integrally extended from the urine collector 20 at the front end thereof, wherein the detachable lid 31 has an inner threaded portion for rotatably coupling at an outer threaded portion of the bottle opening 11 of the bottle 10.

As shown in FIG. 2, the urinal guider 32 is integrally extended from the urine collector 20 to communicate with the funnel channel 21, wherein the urinal guider 32 has an elongated configuration and has an elongated guiding channel 321 to communicate with the funnel channel 21. In particular, the urinal guider 32 is coaxially extended from the detachable lid 31 for ensuring the urinal guider 32 to be inserted into the bottle opening 11 of the bottle 10 when the detachable lid 31 is coupled at the bottle opening 11 of the bottle 10. It is worth mentioning that the urinal guider 32 is coaxially aligned with a centerline of the urine collector 20.

Accordingly, a diameter of the urinal guider 32 is slightly smaller than a diameter of the bottle opening 11 of the bottle 10. In particular, the urinal guider 32 is long enough to extend out of the detachable lid 31 for inserting into the bottle opening 11 of the bottle 10 when the detachable lid 31 is coupled at the bottle opening 11 of the bottle 10. Therefore, after the urinal guider 32 is inserted through the bottle opening 11, the urinal guider 32 not only guides the urine into the bottle 10 but also serves as a shaft to support the urinal collector 20 at the bottle 10, so as to prevent any unwanted movement between the urinal collector 20 and the bottle 10. In other words, the urinal collector 20 is secured to the bottle 10 via the attachment head 30 for preventing the spillage problem during the portable urinal is being used.

It is worth mentioning that after the urinal guider 32 is inserted through the bottle opening 11, the bottle opening 11 of the bottle 10 is not contacted with any urine during use. Therefore, it is sanitary for the user put the bottle cap 12 back to the bottle 10 to close and seal the bottle opening 11 thereof.

As shown in FIG. 2, the attachment head 30 further comprises a bottle retainer 33 forwardly extended for biasing against an exterior wall of the bottle 10 when the detachable lid 31 is coupled at the bottle opening 11 of the bottle 10 so as to prevent an unintentional movement between the urine collector 20 and the bottle 10. In particular, the bottle retainer 33 is formed in conical shape, wherein a diameter of the bottle retainer 33 is gradually increased toward a free edge thereof.

Preferably, the bottle retainer 33 is integrally extended from a peripheral wall of the urine collector 20, such that when the detachable lid 31 is coupled at the bottle opening 11 of the bottle 10, the free edge of the bottle retainer 33 will press against the exterior wall of the bottle 10. In other words, the portable urinal provides three different retention structures to secure the urine collector 20 with the bottle 10, wherein the three retention structures are formed by coupling the detachable lid 31 at the bottle opening 11, by inserting the urinal guider 32 into the bottle opening 11, and by biasing the bottle retainer 33 against the exterior wall of the bottle 10. It is appreciated that the bottle retainer 33 can be detachably coupled at the peripheral wall of the urine collector 20 via any existing detachably fastening structure such as threaded structure.

Figure 3:
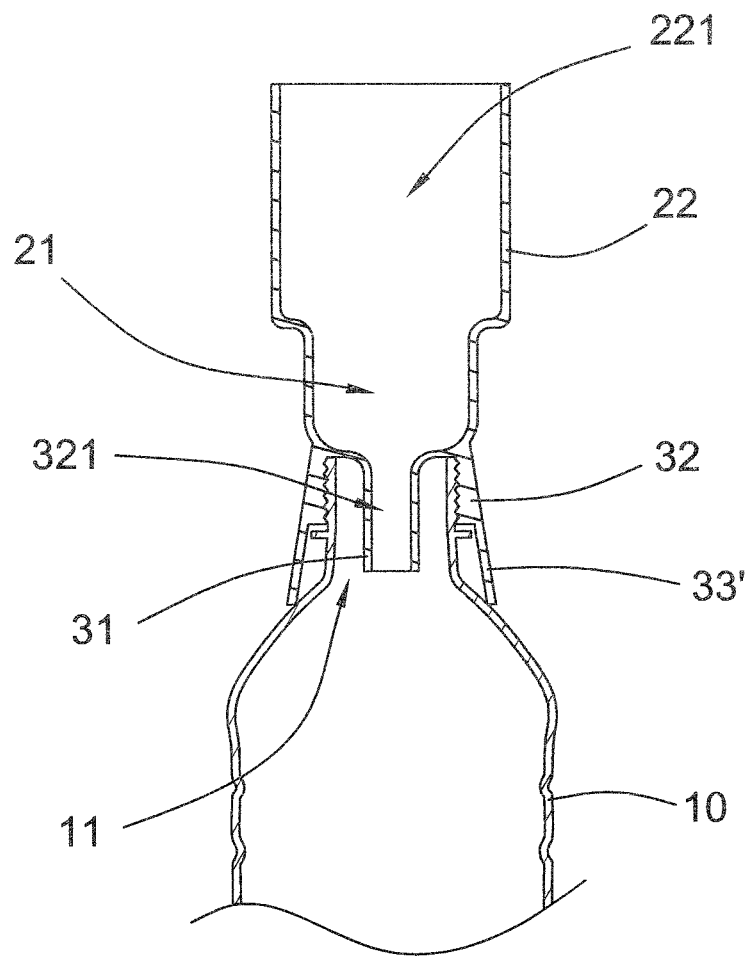
FIG. 3 illustrates an alternative mode of the bottle retainer of the portable urinal according to the above preferred embodiment of the present invention.

FIG. 3 illustrates an alternative mode of the bottle retainer 33' which is integrally extended from a peripheral edge of the detachable lid 31. In other words, when the detachable lid 31 is coupled at the bottle opening 11 of the bottle 10, the free edge of the bottle retainer 33' will press against the exterior wall of the bottle 10 at the same time.

Accordingly, the portable urinal of the present invention can be made of disposable and/or re-cycling material. The portable urinal can be re-usable by rinsing the urine collector 20 after use. It is worth mentioning that the user is able to rinse the urine collector 20 after the urine is collected in the bottle 10 and before the urine collector 20 is detached from the bottle 10. Therefore, the rinsing water will also be collected in the bottle 10. Alternatively, the portable urinal of the present invention can be made of disposable material, such that the user is able to dispose the portable urinal after use. In particular, the portable urinal of the instant invention can be manufactured by plastic mold injection to lower the manufacturing cost thereof. It is worth mentioning that the attachment head 30 is integrated with the urine collector 20 to prevent any spillage or leakage problem during the portable urinal is being used. Therefore, the portable urinal of the present invention provides an economic and efficient solution for providing a simple and portable unisex urinal apparatus for the collecting urine in the bottle in a convenient and sanitary manner.

Figure 4:
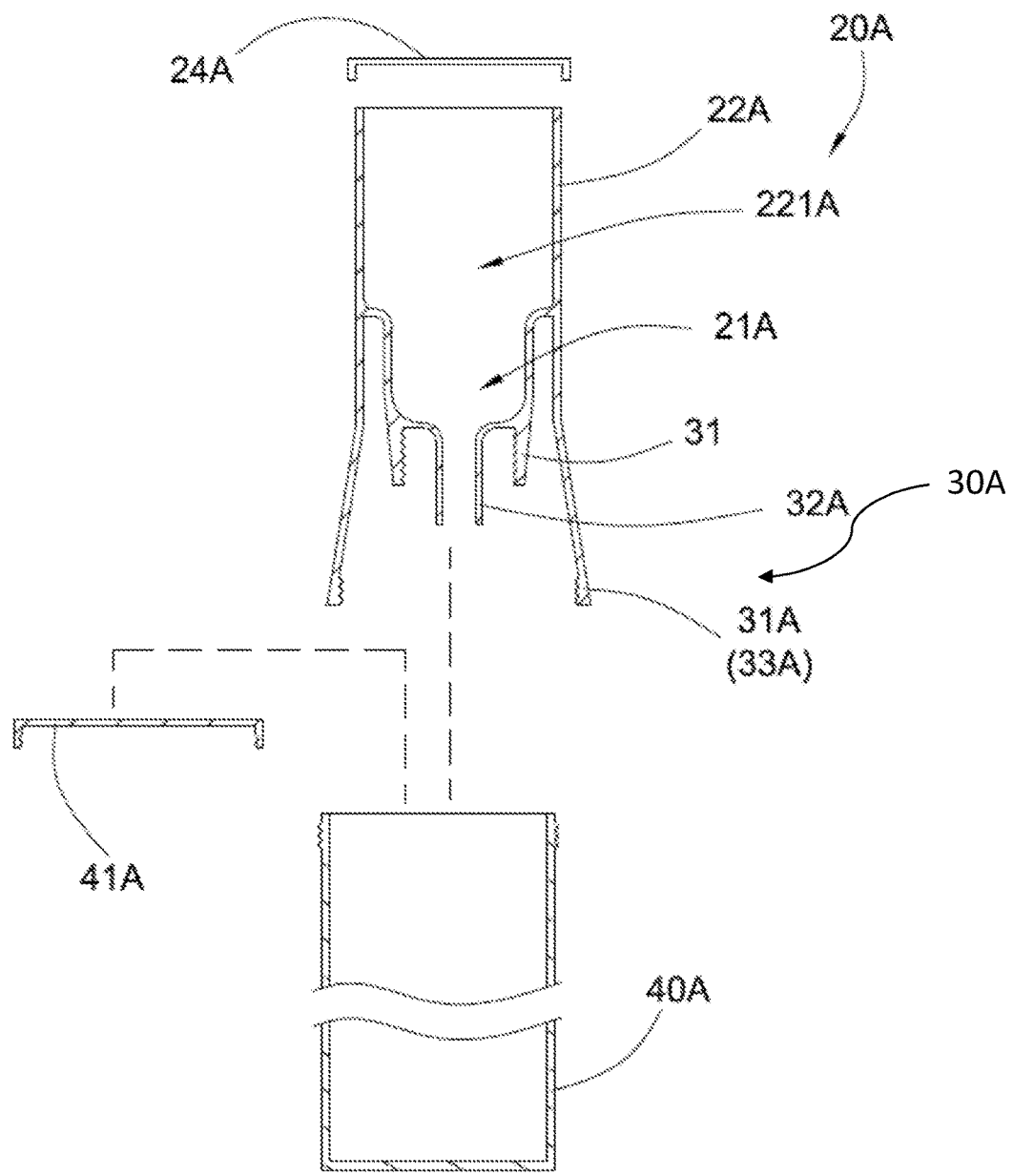
FIG. 4 illustrates a first modification of the portable urinal according to the above preferred embodiment of the present invention.

FIG. 4 illustrates a modification of the portable urinal, which comprises an urine collector 20A and an attachment head 30A similar to the above preferred embodiment, wherein the portable urinal further comprises an urine collecting cup 40A detachably coupled to the urine collector 20A via the attachment head 30A.

According to the modification, the urine collector 20A, having the same structural configuration of the above preferred embodiment, has a funnel channel 21A for receiving urine expelled by a user. The urine collector 20A further comprises a tubular handheld member 22A having an elongated urine channel 221A and defining a portion integrated with the funnel channel 21A. The urine collector 20A further comprises a funnel member 23 (as shown in FIG. 1) detachably coupled at the handheld member 22A for being placed at the urinating orifice of the female user. It is appreciated that the funnel member 23 can be integrally extended from the handheld member 22A as a one piece integrated urine collector. The urine collector 20A further comprises a detachable cap 24A detachably coupled at the handheld member 22A at the rear end to selectively close the funnel channel 21A. It is worth mentioning that the detachable cap 24A can also be used for detachably coupling at the handheld member 22 of the above preferred embodiment.

Accordingly, the attachment head 30A comprises a detachable lid 31A and a tubular urinal guider 32A. The detachable lid 31A is extended from the urine collector 20A and is detachably coupled at the urine collecting cup 40A. The urinal guider 32A is extended from the detachable lid 31A to insert into the urine collecting cup 40A when the detachable lid 31A is coupled at the urine collecting cup 40A so as to guide the urine into the urine collecting cup 40A from the funnel channel 21A.

As shown in FIG. 4, the detachable lid 31A is integrally extended from the urine collector 20A at the front end thereof, wherein the detachable lid 31A has an inner threaded portion for rotatably coupling at an outer threaded portion of the urine collecting cup 40A.

The urinal guider 32A is integrally extended from the urine collector 20A to communicate with the funnel channel 21A, wherein the urinal guider 32A has an elongated configuration and has an elongated guiding channel 321A to communicate with the funnel channel 21A. In particular, the urinal guider 32A is coaxially extended from the detachable lid 31A for ensuring the urinal guider 32A to be inserted into the urine collecting cup 40A when the detachable lid 31A is coupled at the urine collecting cup 40A.

According to the modification, the detachable lid 31A serves as the bottle retainer 33A integrally and forwardly extended from the peripheral wall of the urine collector 20A for detachably coupling with a top opening of the urine collecting cup 40A. A cup lid 41A is detachably coupled and sealed at the top opening of the urine collecting cup 40A.

It should be appreciated that the detachable lid 31 of the preferred embodiment and the detachable lid 31A of the modification are coexist that the portable urine of the present invention can be selectively coupled to the bottle 10 or the urine collecting cup 40A. It is worth mentioning that when the detachable lid 31 is coupled at the bottle opening 11 of the bottle 10, the detachable lid 31A, i.e. the bottle retainer 33, will bias against the exterior wall of the bottle 10. After use, the bottle cap 12 can be coupled at the bottle opening 12 of the bottle 10 to contain the urine therein. The bottle retainer 33 will serve as the detachable lid 31A being coupled at the urine collecting cup 40A. After use, the cup lid 41A can be coupled at the top opening of the urine collecting cup 40A to contain the urine therein. Therefore, the user is able to select which container, the bottle 10 or the urine collecting cup 40A, to be detachably coupled with the urine collector 20A.

Figure 5:
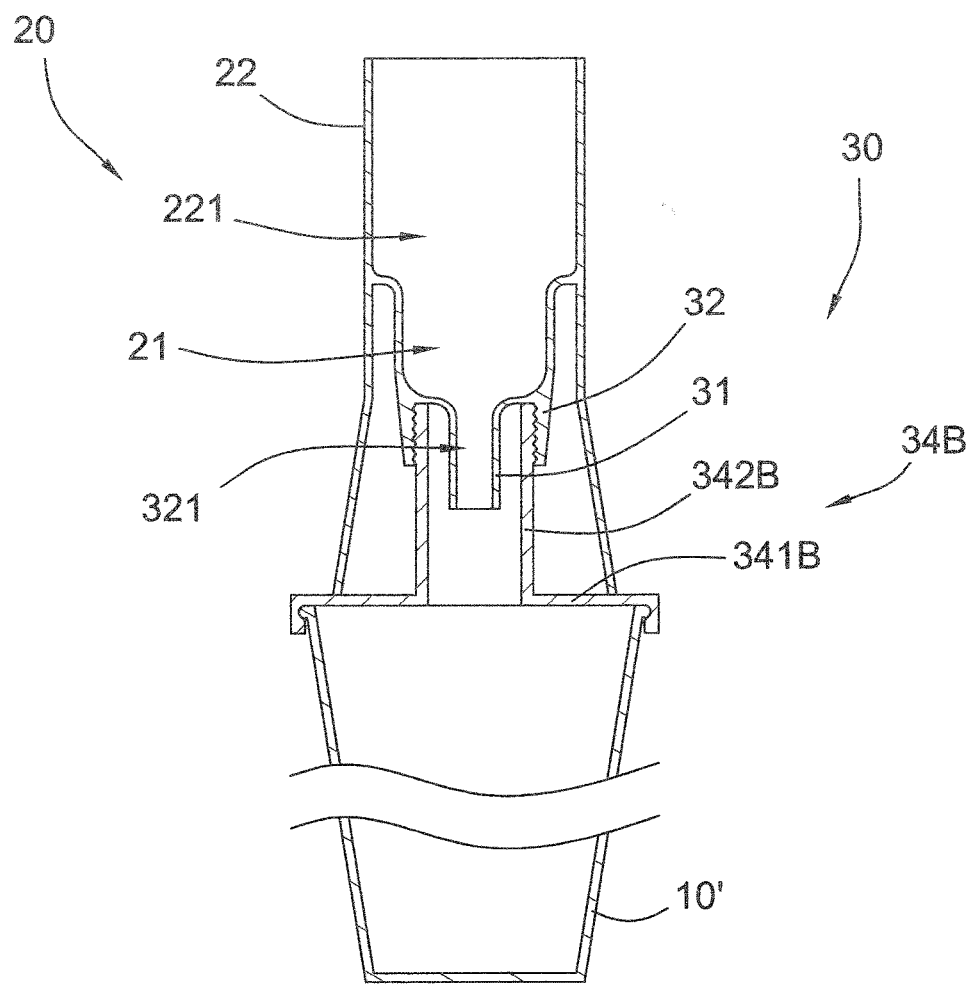
FIG. 5 illustrates a second modification of the portable urinal according to the above preferred embodiment of the present invention.

FIG. 5 illustrates another modification of the portable urinal, wherein the attachment head 30 further comprises a cup adapter 34B for detachably coupling with a disposable cup 10'. Accordingly, the disposable cup 10' can be a soft drink cup from any fast-food restaurant. The cup adapter 34B comprises a lid panel 341B adapted for detachably coupling at an opening rim of the disposable cup 10', and an opening fastener 342B upwardly extended from the lid panel 341B to detachably couple with the detachable lid 31. Accordingly, the opening fastener 342B has a tubular configuration matching with the bottle opening 12 of the bottle 10. In other words, the inner threaded portion of the detachable lid 31 is rotatably engaged with an outer threaded portion of the opening fastener 342B or is rotatably engaged with the outer threaded portion of the bottle opening 12 of the bottle 10. In case the user cannot find any bottle, the cup adapter 34B can be detachably coupled to the urine collector 20 for detachably coupling to the disposable cup 10'.

It is worth mentioning that when the urine collecting cup 40A is configured to have the same opening size of the disposable cup 10', the detachable lid 31A can be detachably coupled with the disposable cup 10' without the cup adapter 34B. Therefore, the user is able to select which container, the bottle 10, the urine collecting cup 40A, or the disposable cup 10', to be detachably coupled with the urine collector 20. It is worth mentioning again that the bottle 10 can be coupled by the detachable lid 31. The urine collecting cup 40A can be coupled by the detachable lid 31A or the cup adapter 34B. The disposable cup 10' can be coupled by the detachable lid 31A or the cup adapter 34B.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:
1. A portable urinal for coupling with a bottle having a bottle opening, comprising:
an urine collector having a funnel channel for receiving urine expelled by a user;

an attachment head comprising a detachable lid extended from said urine collector for detachably coupling at a bottle opening of the bottle, and a tubular urinal guider extended from said detachable lid for inserting into the bottle opening of the bottle when said detachable lid is coupled at the bottle opening of the bottle so as to guide the urine into the bottle from said funnel channel; and a bottle retainer forwardly extended for biasing against an exterior wall of the bottle when said detachable lid is coupled at the bottle opening of the bottle so as to prevent an unintentional movement between said urine collector and the bottle.

2. The portable urinal, as recited in claim 1, wherein said urinal guider is coaxially extended from said detachable lid for ensuring said urinal guider to be inserted into the bottle opening of the bottle when said detachable lid is coupled at the bottle opening of the bottle, wherein said urinal guider is integrally extended from said urine collector to communicate with said funnel channel and is extended out of said detachable lid for inserting into the bottle opening of the bottle when said detachable lid is coupled at the bottle opening of the bottle, wherein said detachable lid is integrally extended from said urine collector and has an inner threaded portion for rotatably coupling at an outer threaded portion of the bottle opening of the bottle.

3. The portable urinal, as recited in claim 1, wherein said bottle retainer is formed in a conical shape and is integrally extended from a peripheral wall of said urine collector.

4. The portable urinal, as recited in claim 2, wherein said bottle retainer is formed in a conical shape and is integrally extended from a peripheral wall of said urine collector.

5. The portable urinal, as recited in claim 1, wherein said bottle retainer is formed in a conical shape and is integrally extended from a peripheral edge of said detachable lid.

6. The portable urinal, as recited in claim 2, wherein said bottle retainer is formed in a conical shape and is integrally extended from a peripheral edge of said detachable lid.

7. The portable urinal, as recited in claim 4, wherein said urine collector further comprises a tubular handheld member having an elongated urine channel to communicate with said funnel channel, wherein said handheld member is arranged for being held at an urinating orifice of a male user.

8. The portable urinal, as recited in claim 6, wherein said urine collector further comprises a tubular handheld member having an elongated urine channel to communicate with said funnel channel, wherein said handheld member is arranged for being held at an urinating orifice of a male user.

9. The portable urinal, as recited in claim 7, wherein said urine collector further comprises a funnel member detachably coupled at said handheld member for being placed at an urinating orifice of a female user.

10. The portable urinal, as recited in claim 8, wherein said urine collector further comprises a funnel member detachably coupled at said handheld member for being placed at an urinating orifice of a female user.

* * * * *